United States Patent [19]
Ellis et al.

[11] Patent Number: 5,030,419
[45] Date of Patent: Jul. 9, 1991

[54] WASTEWATER POLLUTANT SENSOR

[76] Inventors: Arthur B. Ellis, 2021 Kendall Ave., Madison, Wis. 53705; Elizabeth R. M. Luebker, 766 S. Gammon Rd. #108, Madison, Wis. 53719; Larry K. Leung, 119 Ski Ct., Madison, Wis. 53713; George C. Lisensky, 1234 Partridge Ave., Beloit, Wis. 53511

[21] Appl. No.: 537,822

[22] Filed: Jun. 14, 1990

[51] Int. Cl.⁵ .................... G01N 31/00; G01N 21/76; G01J 00/00; F21K 2/00
[52] U.S. Cl. .................... 422/82.09; 422/82.05; 422/82.08; 436/172; 250/370.01; 250/462.1
[58] Field of Search .................... 422/58, 82.01, 82.02, 422/82.05, 82.08, 82.09; 436/172; 250/370.01, 462.1

[56] References Cited

U.S. PATENT DOCUMENTS

| | | | |
|---|---|---|---|
| 3,433,964 | 3/1969 | Morrison et al. | 422/82.05 |
| 4,645,932 | 2/1987 | Ellis et al. | 250/370.01 |
| 4,710,476 | 12/1987 | Ellis et al. | 436/172 |
| 4,752,588 | 6/1988 | Ellis et al. | 436/172 |

Primary Examiner—Robert J. Warden
Assistant Examiner—Theresa A. Trembley
Attorney, Agent, or Firm—James E. Brunton

[57] ABSTRACT

The presence of certain chemicals on the emitting surface of the surface-derivatized photoluminescent semiconductor alters the characteristics of radiation emitted from said surface. This alteration is used to indicate the presence of those chemicals in the environment.

14 Claims, 1 Drawing Sheet

WASTEWATER POLLUTANT SENSOR

BACKGROUND OF THE INVENTION

1. Field of the Invention

The present invention relates generally to optically-coupled chemical sensing devices and to processes for detecting the presence of certain classes of chemical compounds. More particularly the invention concerns an apparatus for use in sensing pollutants in water such as wastewater.

2. Discussion of the Invention

Introduction

Electroluminescence occurs in semiconductor materials that are capable of emitting visible or near visible radiation when an electrical current passes through the semiconductor. Photoluminescence can also occur in these materials. If external light is used to excite the semiconductor, a characteristic wavelength of light is emitted. These characteristic wavelengths vary amongst different photoluminescent semiconductors and can be varied in a single semiconductor by doping or changing the composition of the material.

Amongst the various studies on the luminescence of photostimulated or electroluminescent materials is "Luminescent Photoelectrochemical Cells", Streckert, H. H., Tong, J. and Ellis. A. B., J. Am Chem. Soc. Vol 104, No. 2, 1982, pp 581–588. It is noted therein that the intensity of light emitted by electroluminescence and photoluminescence varies directly with the applied voltage. The efficiency of charge transfer and good electrical contact at the surface is also noted as important in the efficiency of the process.

U.S. Pat. No. 4,780,643 discloses semiconductor electrodes having multicolor luminescence. These semiconductors comprise solid-state solutions of three elements that vary in a vertically anisotropic manner. The preferred solid-state solutions are of cadmium, sulfur and selenium.

U.S. Pat. No. 4,211,586 discloses a method of forming a multicolor light-emitting array of diodes. The diodes are formed by differentially etching a graded n-type semiconductor and diffusing a p-type dopant into the surface of the n-type semiconductor to form a p-n junction diode.

U.S. Pat. No. 4,645,932 discloses an apparatus for detecting the presence of certain chemical compounds comprising a photoluminescent semiconductor having a metal coating on a radiation-emitting surface of the semiconductor, a source of actinic radiation that can impinge on the radiation-emitting surface of the semiconductor, and a means for detecting changes in the characteristics of radiation emitted from said radiation-emitting surface. The absorption of hydrogen into the metal layer is suggested as varying the height of the Schottky barrier of the diode and causing a change in spectral characteristics of the radiation emitted.

U.S. Pat. No. 4,710,476 discloses an optically-coupled sensing apparatus of a photoluminescent semiconductor, a source of actinic radiation that can impinge on a radiation-emitting surface of the semiconductor, and a means for detecting changes in the characteristics of the radiation emitted from the radiation-emitting surface. The radiation-emitting surface has reacted thereon a compound capable of undergoing oxidation and/or reduction, the redox product of which reacted compound has a vertical charge distribution therein with respect to the radiation-emitting surface.

U.S. Pat. No. 4,752,588 discloses an optically-coupled sensing apparatus of a photoluminescent semiconductor, a source of actinic radiation that can impinge on a radiation-emitting surface of the semiconductor, and a means for detecting changes in the characteristics of the radiation emitted from the radiation-emitting surface. The radiation-emitting surface has reacted thereon a compound is capable of bonding to certain gases, undergoing oxidative addition and/or reductive elimination reactions, resulting in a change in the vertical charge distribution with respect to the radiation-emitting surface.

SUMMARY OF THE INVENTION

The present invention also describes an optically-coupled sensing apparatus of a photoluminescent semiconductor, a source of actinic radiation that can impinge on a radiation-emitting surface of the semiconductor, and a means for detecting changes in the characteristics of the radiation emitted from the radiation-emitting surface. However, in the apparatus of the present invention the radiation-emitting surface of the semiconductor uniquely has reacted thereon a compound capable of bonding to certain solutes in aqueous solution through the formation of weak adducts, resulting in a change in the distribution of surface electronic states (surface states) and thus in a change in the photoluminescence of the semiconductor. Accordingly, the apparatus of the invention is extremely useful in detecting pollutants in aqueous solutions.

DESCRIPTION OF THE INVENTION

Figure 1:
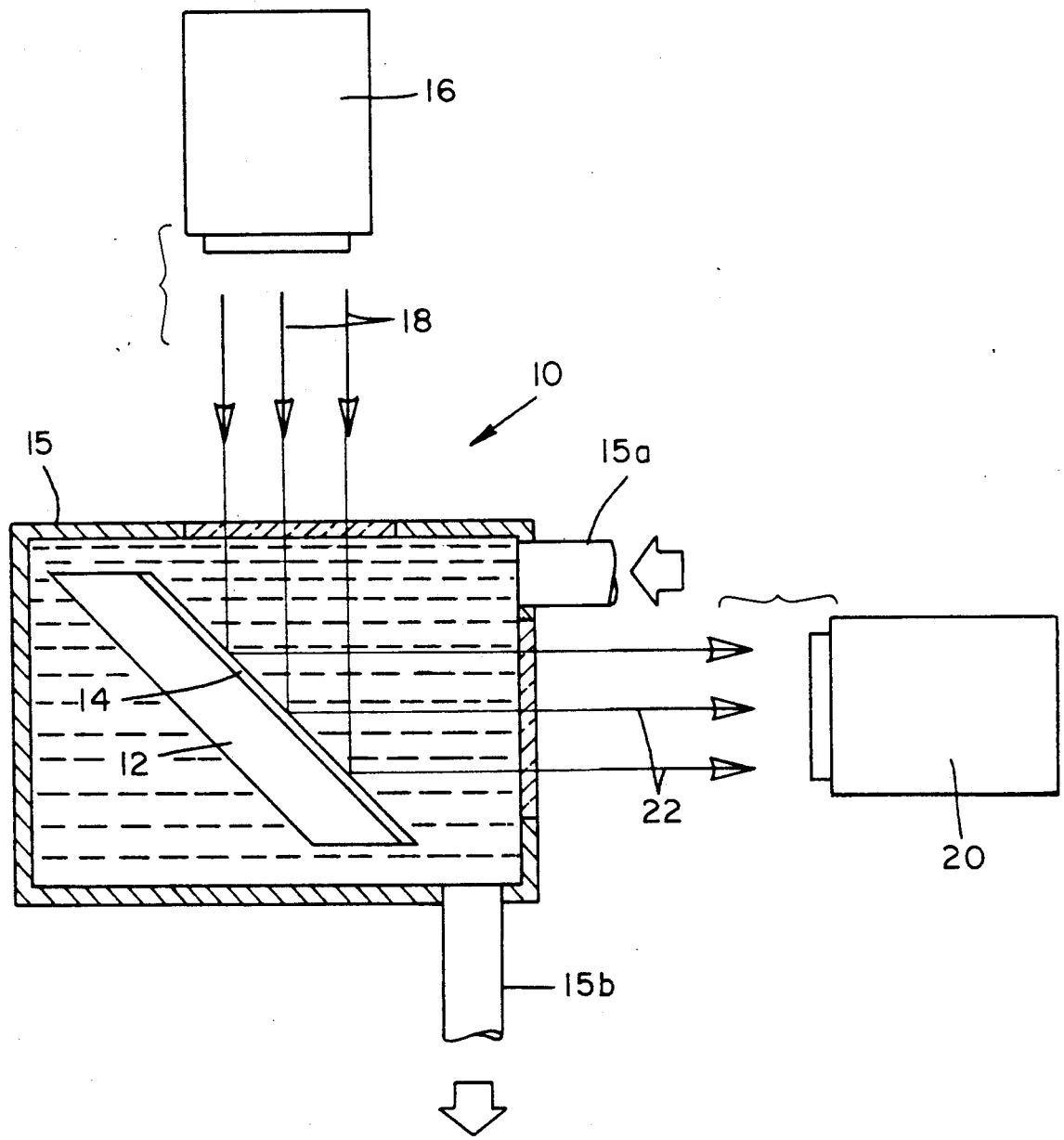
FIG. 1 is a schematic representation of one form of the apparatus of the present invention.

Referring to the drawing, one form of the apparatus of the present invention, generally designated by the numeral 10, comprises a photoluminescent semiconductor layer 12 having a surface layer 14. Surface layer 14 is uniquely capable of bonding to certain aqueous solutes such as a surface having bonded thereto a compound capable of forming weak adducts. In the embodiment of the invention shown in FIG. 1, semiconductor layer 12 and surface layer 14 are mounted internally of a container, or tank, 15 for containing an aqueous solution and having a fluid inlet 15a and a fluid outlet 15b. An externally mounted source 16 of actinic radiation 18 is provided to direct radiation 18 toward the semiconductor layer 14. An externally mounted detector 20 is provided to detect changes in the radiation 22 emitted from the semiconductor 12.

The apparatus of the present invention uses the modification of electric fields in compounds on the surface of photoluminescent semiconductors to alter or modulate the electric field of the semiconductor. The modulation of the electric field, in turn, alters the photoluminescence of the semiconductor, and this alteration can readily be detected by the sensing means.

The compound can be coated or preferably reacted onto the surface of the semiconductor. The coated material or reacted compound must be capable of participating in adduct-induced changes in surface state distribution through its chemical interaction with aqueous solutes. If these adducts are weakly bound, the reactions are rapidly reversible so that photoluminescence changes resulting from adduct formation can be used to monitor the presence of the aqueous solute "on-line" as a dynamic process.

Photoluminescent semiconductors of the character used in the apparatus of the invention are well known in the art. They are generally solid-state solutions of at least two or three elements which, when stimulated by actinic radiation, emit radiation. Both the actinic and emitted radiation are generally visible or near-visible radiation (300-900 nm). When the semiconductor coating bonds to a solute present in aqueous media that alters the surface state distribution by adduct formation, the electric field in the semiconductor surface and the photoluminescence of the semiconductor has been found to be altered. Variations in photoluminescence are an indication of the presence of species that are involved in bonding to the coating.

Particularly useful n-type semiconductors that can be used to form the detectors according to the present invention are n-GaAs, n-$GaAs_xP_{1-x}$ (where x is from 0 to 1) and n- and p-InP. The surface compound that undergoes adduct formation reactions can be created on the elements according to standard manufacturing techniques.

The functional apparatus for actually using this phenomenon for detecting the presence of aqueous solutes capable of adduct formation with the semiconductor coating would have at least the following three components: the semiconductor (and the coating), a source of actinic radiation directed at the radiation-emitting surface of the sensor or structure formed by the coating on the semiconductor, and an optical detector. For the coated photoluminescent semiconductor, the sensor or structure is simply a piece of the semiconductor the surface of which has been coated with a material that forms adducts with desired aqueous solutes leading to changes in surface state distribution. The coating material must, of course, be insoluble in the aqueous medium of interest. The actinic radiation source may be merely an opening exposing the sensor or structure to available light (room light, sun light, etc.) or it may be any internal source of radiation such as a light bulb, light emitting diode, or laser. The detector can be selected from amongst the many commercially available radiometers, its selection being primarily dependent upon the ultimate sensitivity desired. If desired, fiber optics can be used to carry the actinic radiation to the sensor or to carry emitted radiation away from the sensor. The sensor can be mounted in a static container or in a dynamic container of the character shown in the drawing.

EXAMPLE 1

Samples of n-GaAs were prepared for coating by etching in 1:8:500 $H_2SO_4:30\%H_2O_2:H_2O$ until a highly photoluminescent surface was observed. A drop or two of 20% aqueous $(NH_4)S_2$ (ammonium sulfide) was placed on the surface and evaporated in a stream of air; this procedure was repeated until a highly photoluminescent surface was observed.

When the sensor was placed in tank 15 and was illuminated with ultrabandgap light, the bandgap photoluminescence (PL) of the GaAs substrate (865-870 nm in the near IR) was sensitive to the presence of small concentrations of amines dissolved in the water flowing through the tank which caused the PL to decline by up to 30%. The PL intensity returned to its original value when pure distilled water was caused to flow through the tank 15. Both changes occurred on the time scale of seconds.

EXAMPLE 2

Example 1 was repeated except that soluble ammonium salts (nitrate and sulfate) were added to pure distilled water flowing through tank 15 causing the PL intensity to increase by up to 30%. These changes too were reversible.

EXAMPLE 3

Example 1 was repeated causing influent and effluent from a wastewater treatment plant to flow through tank 15. The effluent yielded about the same PL intensity as pure distilled water. The PL intensity in the presence of the influent was increased by up to 55% relative to the effluent signal, reflecting the presence of dissolved ammonium ions, whose concentration was independently determined. Using standard techniques, a working calibration curve can be constructed so that PL intensity can be related directly to the concentration of ammonium ions in aqueous solution.

In the apparatus of the invention, the semiconductor can comprise a solid state solution of at least two elements selected from the group consisting of gallium and arsenic; gallium, arsenic and phosphorus; gallium and phosphorus; and indium and phosphorus.

It is to be observed that many semiconductors, including GaAs, are unstable when irradiated in aqueous solution (Ellis et al., Journal of the American Chemical Society, vol. 99, pg 2848, 1977) so that the stability of the ammonium sulfide-coated GaAs would not have been anticipated. The concept of exposing GaAs to aqueous solutions containing chalcogenide (sulfide, selenide, telluride) was discussed in this same article, although sulfide alone did not stabilize GaAs electrodes.

It should also be noted that coating GaAs with sodium sulfide and ammonium sulfide salts has been carried out extensively recently to improve the electrical performance of purely solid-state electronic devices. Leading references include C. Sandroff et al. Applied Physics Letters, vol. 53, pg. 1059, 1988; B. A. Cowens et al. same journal, vol. 54, pg. 365, 1989; M. S. Carpenter et al. same journal, vol. 52, pg. 2157, 1988.

As discussed in the preceding paragraphs and in the examples, the photoluminescent substrates useful in the practice of the present invention are coated surfaces having compounds reacted thereto which are capable of undergoing adduct formation with aqueous solutes to produce a change in surface state distribution leading to changes in electric field thickness and PL intensity. The apparatus of the invention, while particularly useful in the on-line dynamic detection of pollutants in waste water, can be used in the static or dynamic analysis of numerous aqueous solutions.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

We claim:

1. An apparatus for detecting the presence of chemical compounds comprising:

(a) a photoluminescent semiconductor having a radiation emitting surface and having a reacted material bonded to said radiation-emitting surface of said semiconductor, said reacted material being capable of engaging in adduct formation with aqueous solutes to produce a reaction product bonded to said radiation-emitting surface, said reacted material causing a surface state distribution and said reaction product altering the surface state distribution with respect to the radiation-emitting surface, said surface state distribution being capable of altering an electric field in said semiconductor;

(b) a source of actinic radiation that can impinge on said radiation-emitting surface of the semiconductor; and (c) a means for detecting changes in the radiation emitted from said radiation-emitting surface.

2. The apparatus of claim 1 wherein said source of actinic radiation comprises visible light.

3. The apparatus of claim 1 wherein said semiconductor comprises a solid-state solution of at least two elements selected from the group consisting of:
   (a) gallium and arsenic;
   (b) gallium, arsenic, and phosphorus;
   (c) gallium and phosphorus; and
   (d) indium and phosphorus.

4. The apparatus of claim 3 wherein said means for detecting changes in the characteristics of the radiation is a radiometer.

5. The apparatus of claim 3 wherein said semiconductor has a coating of said reactive material containing a sulfide salt that is insoluable in the aqueous solution of interest.

6. The apparatus of claim 1 wherein said means for detecting changes in the characteristics of the radiation is a radiometer.

7. The apparatus of claim 6 wherein said source of actinic radiation comprises visible light.

8. The apparatus of claim 6 wherein said semiconductor has a coating of said reactive material containing a sulfide salt that is insoluble in the aqueous solution of interest.

9. The apparatus of claim 8 wherein said source of actinic radiation comprises visible light.

10. An apparatus for detecting the presence of chemical compounds comprising:
    (a) a photoluminescent semiconductor having a reacted material on a radiation emitting surface thereof, said reacted material bonding to various aqueous solutes through adduct formation to produce a product bonded to said radiation-emitting surface, said reacted material having a surface state distribution which is vertical with respect to the radiation-emitting surface, said surface state distribution being capable of altering an electric field in said semiconductor;
    (b) a source of actinic radiation that can impinge on said radiation-emitting surface of the semiconductor; and
    (c) a means for detecting changes in the radiation emitting from said radiation-emitting surface.

11. A process for detecting the presence of chemical components comprising the steps of:
    (a) providing a photoluminescent semiconductor having at least one radiation-emitting surface having a reacted material bonded to said radiation-emitting surface, said reacted material being capable of engaging in adduct formation with aqueous solutes to alter the distribution with respect to the radiation-emitting surface, said surface state distribution being capable of altering an electric field in said semiconductor:
    (b) irradiating said semiconductor with actinic radiation;
    (c) observing the characteristics of radiation emitted from said semiconductor;
    (d) exposing said surface to an aqueous environment having chemical compounds capable of reacting with said reacted material by adduct formation; and
    (e) detecting any changes in the radiation emitted from said surface, which thereby indicates the presence of chemical components.

12. The process of claim 11 wherein said actinic radiation is ambient light.

13. The process of claim 11 wherein light from a light bulb, laser, or light emitting diode provides said actinic radiation.

14. A process for detecting the presence of chemical components comprising the steps;
    (a) providing a photoluminescent semiconductor having at least one radiation-emitting surface, said surface being capable of bonding with aqueous solutes to produce an adduct or reduct which will alter the surface state distribution with respect to the radiation-emitting surface, said surface state distribution being capable of altering the electric field in said semiconductor;
    (b) irradiating said semiconductor with actinic radiation;
    (c) observing the characteristics of radiation emitted from said semiconductor;
    (d) exposing said surface to an aqueous environment having chemical compounds capable of bonding with said surface by adduct formation; and
    (e) detecting any changes in the characteristics of radiation emitted from said surface, which thereby indicates the presence of chemical components.

* * * * *